United States Patent
Goel et al.

(10) Patent No.: US 11,766,281 B2
(45) Date of Patent: Sep. 26, 2023

(54) SPINAL FIXATION SYSTEM

(71) Applicant: NuVasive, Inc., San Diego, CA (US)

(72) Inventors: Prakhar Goel, San Diego, CA (US);
Scott Lish, Oceanside, CA (US);
Fernando Olea, San Diego, CA (US);
Conrad Tyler Hammann, Carlsbad, CA (US)

(73) Assignee: NuVasive, Inc., San Diego, CA (US)

( * ) Notice: Subject to any disclaimer, the term of this patent is extended or adjusted under 35 U.S.C. 154(b) by 135 days.

(21) Appl. No.: 17/454,427

(22) Filed: Nov. 10, 2021

(65) Prior Publication Data

US 2022/0061896 A1 Mar. 3, 2022

Related U.S. Application Data

(63) Continuation of application No. 16/512,698, filed on Jul. 16, 2019, now Pat. No. 11,197,697, which is a continuation of application No. 15/829,955, filed on Dec. 3, 2017, now Pat. No. 10,398,481.

(60) Provisional application No. 62/403,501, filed on Oct. 3, 2016.

(51) Int. Cl.
*A61B 17/70* (2006.01)
(52) U.S. Cl.
CPC ...... *A61B 17/7086* (2013.01); *A61B 17/7002* (2013.01); *A61B 17/7032* (2013.01)
(58) Field of Classification Search
CPC . A61B 17/70; A61B 17/7083; A61B 17/7085; A61B 17/7086; A61B 17/7088; A61B 17/7091

USPC ............................................ 606/86 A, 279
See application file for complete search history.

(56) References Cited

U.S. PATENT DOCUMENTS

| | | | |
|---|---|---|---|
| 4,282,217 | A | 8/1981 | Baglioni |
| 4,316,169 | A | 2/1982 | Teranishi |
| 4,450,899 | A | 5/1984 | Jakobsson |
| 5,217,497 | A | 6/1993 | Mehdian |
| 5,360,431 | A | 11/1994 | Puno |
| 5,474,555 | A | 12/1995 | Puno |
| 5,496,321 | A | 3/1996 | Puno |
| 5,681,319 | A | 10/1997 | Biedermann |
| 5,716,356 | A | 2/1998 | Biedermann |
| 5,910,141 | A | 6/1999 | Morrison |

(Continued)

FOREIGN PATENT DOCUMENTS

| | | |
|---|---|---|
| DE | 202012102895 U1 | 8/2012 |
| EP | 1891904 A1 | 2/2008 |

(Continued)

*Primary Examiner* — Eduardo C Robert
*Assistant Examiner* — Christina Negrellirodriguez
(74) *Attorney, Agent, or Firm* — Hoffman Warnick LLC

(57) ABSTRACT

This application describes surgical instruments and implants, including a rod reduction instrument, for building a posterior fixation construct across one or more segments of the spinal column. Extension guides are provided that attach to bone anchors implanted within the spine. The extension guides have a guide channel that align with a rod channel in the anchor to help direct the rod to the anchor. The rod reducer may be passed through the interior of the guide assemblies with a distal end arranged in a first position allowing the distal end to pass through the guide. Once through the guide the distal end may be expanded to provide dual contact on the rod at each end of the bone anchor rod channel.

20 Claims, 12 Drawing Sheets

(56) References Cited

U.S. PATENT DOCUMENTS

| | | |
|---|---|---|
| 5,941,885 A | 8/1999 | Jackson |
| 6,059,786 A | 5/2000 | Jackson |
| 6,139,549 A | 10/2000 | Keller |
| 6,179,841 B1 | 1/2001 | Jackson |
| 6,189,422 B1 | 2/2001 | Stihl |
| 6,224,598 B1 | 5/2001 | Jackson |
| 6,251,112 B1 | 6/2001 | Jackson |
| 6,258,090 B1 | 7/2001 | Jackson |
| 6,379,356 B1 | 4/2002 | Jackson |
| 6,440,132 B1 | 8/2002 | Jackson |
| 6,440,133 B1 | 8/2002 | Beale |
| 6,485,494 B1 | 11/2002 | Haider |
| 6,530,929 B1 | 3/2003 | Justis |
| 6,554,834 B1 | 4/2003 | Crozet |
| 6,648,888 B1 | 11/2003 | Shluzas |
| 6,723,100 B2 | 4/2004 | Biedermann |
| 6,726,687 B2 | 4/2004 | Jackson |
| 6,743,231 B1 | 6/2004 | Gray |
| 6,884,244 B1 | 4/2005 | Jackson |
| 7,008,422 B2 | 3/2006 | Foley |
| 7,011,660 B2 | 3/2006 | Sherman |
| 7,073,415 B2 | 7/2006 | Casutt |
| 7,094,239 B1 | 8/2006 | Michelson |
| 7,160,300 B2 | 1/2007 | Jackson |
| 7,179,261 B2 | 2/2007 | Sicvol |
| 7,188,626 B2 | 3/2007 | Foley |
| 7,204,838 B2 | 4/2007 | Jackson |
| 7,250,052 B2 | 7/2007 | Landry |
| 7,278,995 B2 | 10/2007 | Nichols |
| D560,128 S | 1/2008 | Diederich |
| 7,470,279 B2 | 12/2008 | Jackson |
| 7,476,240 B2 | 1/2009 | Raymond |
| 7,491,208 B2 | 2/2009 | Pond |
| 7,491,218 B2 | 2/2009 | Landry |
| 7,520,879 B2 | 4/2009 | Justis |
| 7,527,638 B2 | 5/2009 | Anderson |
| 7,563,264 B2 | 7/2009 | Landry |
| 7,574,318 B2 | 8/2009 | Hsieh |
| 7,588,575 B2 | 9/2009 | Colleran |
| 7,588,588 B2 | 9/2009 | Spitler |
| 7,608,081 B2 | 10/2009 | Abdelgany |
| 7,618,422 B2 | 11/2009 | Goodwin |
| 7,621,918 B2 | 11/2009 | Jackson |
| 7,648,521 B2 | 1/2010 | Hestad |
| 7,651,502 B2 | 1/2010 | Jackson |
| 7,678,139 B2 | 3/2010 | Garamszegi |
| 7,691,132 B2 | 4/2010 | Landry |
| 7,708,743 B2 | 5/2010 | Anderson |
| 7,708,763 B2 | 5/2010 | Selover |
| 7,717,921 B2 | 5/2010 | Rezach |
| 7,717,944 B2 | 5/2010 | Foley |
| 7,744,629 B2 | 6/2010 | Hestad |
| 7,749,233 B2 | 7/2010 | Farr |
| 7,758,617 B2 | 7/2010 | Iott |
| 7,763,055 B2 | 7/2010 | Foley |
| 7,771,430 B2 | 8/2010 | Jones |
| 7,811,288 B2 | 10/2010 | Jones |
| 7,854,751 B2 | 12/2010 | Sicvol |
| 7,862,595 B2 | 1/2011 | Foley |
| 7,867,259 B2 | 1/2011 | Foley |
| 7,909,835 B2 | 3/2011 | Oribe |
| 7,914,558 B2 | 3/2011 | Landry |
| 7,918,857 B2 | 4/2011 | Dziedzic |
| 7,918,858 B2 | 4/2011 | Stad |
| 7,918,878 B2 | 4/2011 | Songer |
| 7,922,727 B2 | 4/2011 | Songer |
| 7,927,334 B2 | 4/2011 | Miller |
| 7,931,654 B2 | 4/2011 | Jones |
| 7,931,673 B2 | 4/2011 | Hestad |
| 7,947,045 B2 | 5/2011 | Hestad |
| 7,955,355 B2 | 6/2011 | Chin |
| 7,967,821 B2 | 6/2011 | Sicvol |
| 7,985,242 B2 | 7/2011 | Forton |
| 8,002,798 B2 | 8/2011 | Chin |
| 8,034,084 B2 | 10/2011 | Landry |
| 8,052,720 B2 | 11/2011 | Kuester |
| 8,062,340 B2 | 11/2011 | Berrevoets |
| 8,066,739 B2 | 11/2011 | Jackson |
| 8,075,592 B2 | 12/2011 | Landry |
| 8,100,915 B2 | 1/2012 | Jackson |
| 8,100,951 B2 | 1/2012 | Justis |
| 8,105,361 B2 | 1/2012 | Anderson |
| 8,137,355 B2 | 3/2012 | Hestad |
| 8,137,356 B2 | 3/2012 | Hestad |
| 8,137,387 B2 | 3/2012 | Garamszegi |
| 8,152,810 B2 | 4/2012 | Jackson |
| 8,162,948 B2 | 4/2012 | Jackson |
| 8,177,817 B2 | 5/2012 | Fallin |
| 8,192,439 B2 | 6/2012 | Songer |
| 8,192,440 B2 | 6/2012 | Jones |
| 8,231,635 B2 | 7/2012 | Sharifi-Mehr |
| 8,262,662 B2 | 9/2012 | Beardsley |
| 8,273,089 B2 | 9/2012 | Jackson |
| 8,277,491 B2 | 10/2012 | Selover |
| 8,292,892 B2 | 10/2012 | Jackson |
| 8,303,595 B2 | 11/2012 | Jones |
| 8,308,728 B2 | 11/2012 | Iott |
| 8,317,796 B2 | 11/2012 | Stihl |
| 8,361,124 B2 | 1/2013 | Sherman |
| 8,377,067 B2 | 2/2013 | Jackson |
| 8,439,922 B1 * | 5/2013 | Arnold ................. A61B 17/708 606/279 |
| 8,460,300 B2 | 6/2013 | Hestad |
| 8,460,308 B2 | 6/2013 | Marino |
| 8,470,008 B2 | 6/2013 | Dickinson |
| 8,496,685 B2 | 7/2013 | Landry |
| 8,518,082 B2 | 8/2013 | Sicvol |
| 8,608,746 B2 | 12/2013 | Kolb |
| 8,617,427 B2 | 12/2013 | Jiang |
| RE44,813 E | 3/2014 | Beale |
| 8,663,298 B2 | 3/2014 | Keyer |
| 8,679,128 B2 | 3/2014 | Seelig |
| 2002/0072751 A1 | 6/2002 | Jackson |
| 2002/0133159 A1 | 9/2002 | Jackson |
| 2003/0199872 A1 | 10/2003 | Markworth |
| 2003/0224327 A1 | 12/2003 | Constantino |
| 2003/0225408 A1 | 12/2003 | Nichols |
| 2003/0236529 A1 | 12/2003 | Shluzas |
| 2004/0039383 A1 | 2/2004 | Jackson |
| 2004/0049196 A1 | 3/2004 | Jackson |
| 2004/0147937 A1 | 7/2004 | Dunbar |
| 2004/0158247 A1 | 8/2004 | Sitiso |
| 2004/0167523 A1 | 8/2004 | Jackson |
| 2004/0254576 A1 | 12/2004 | Dunbar |
| 2004/0267275 A1 | 12/2004 | Cournoyer |
| 2005/0176468 A1 | 8/2005 | Iacono |
| 2005/0182410 A1 | 8/2005 | Jackson |
| 2005/0192570 A1 | 9/2005 | Jackson |
| 2005/0192579 A1 | 9/2005 | Jackson |
| 2005/0228380 A1 | 10/2005 | Moore |
| 2006/0036254 A1 | 2/2006 | Lim |
| 2006/0069391 A1 | 3/2006 | Jackson |
| 2006/0074418 A1 | 4/2006 | Jackson |
| 2006/0089651 A1 | 4/2006 | Trudeau |
| 2006/0095035 A1 | 5/2006 | Jones |
| 2006/0100622 A1 | 5/2006 | Jackson |
| 2006/0111712 A1 | 5/2006 | Jackson |
| 2006/0111713 A1 | 5/2006 | Jackson |
| 2006/0111715 A1 | 5/2006 | Jackson |
| 2006/0200132 A1 | 9/2006 | Chao |
| 2006/0229614 A1 | 10/2006 | Foley |
| 2006/0247630 A1 | 11/2006 | Iott |
| 2006/0276789 A1 | 12/2006 | Jackson |
| 2006/0293684 A1 | 12/2006 | Shluzas |
| 2006/0293692 A1 | 12/2006 | Whipple |
| 2007/0043378 A1 | 2/2007 | Kumar |
| 2007/0055240 A1 | 3/2007 | Matthis |
| 2007/0065692 A1 | 3/2007 | Ryoo |
| 2007/0213722 A1 | 9/2007 | Jones |
| 2007/0270811 A1 | 11/2007 | Dewey |
| 2007/0288002 A1 | 12/2007 | Carls |
| 2007/0288007 A1 | 12/2007 | Burkus |
| 2007/0299450 A1 | 12/2007 | Her |
| 2008/0009864 A1 | 1/2008 | Forton |

(56) References Cited

U.S. PATENT DOCUMENTS

| | | |
|---|---|---|
| 2008/0015601 A1 | 1/2008 | Castro |
| 2008/0039844 A1 | 2/2008 | Jackson |
| 2008/0045957 A1 | 2/2008 | Wagner |
| 2008/0045970 A1 | 2/2008 | Saidha |
| 2008/0051794 A1 | 2/2008 | Dec |
| 2008/0086132 A1 | 4/2008 | Biedermann |
| 2008/0091213 A1 | 4/2008 | Jackson |
| 2008/0172062 A1 | 7/2008 | Donahue |
| 2008/0234678 A1 | 9/2008 | Gutierrez |
| 2008/0243190 A1 | 10/2008 | Dziedzic |
| 2008/0275456 A1 | 11/2008 | Vonwiller |
| 2008/0288005 A1 | 11/2008 | Jackson |
| 2008/0300638 A1 | 12/2008 | Beardsley |
| 2009/0030419 A1 | 1/2009 | Runco |
| 2009/0030420 A1 | 1/2009 | Runco |
| 2009/0105712 A1 | 4/2009 | Dauster |
| 2009/0157125 A1 | 6/2009 | Hoffman |
| 2009/0174467 A1 | 7/2009 | Kim |
| 2009/0216281 A1 | 8/2009 | Vonwiller |
| 2009/0216328 A1 | 8/2009 | Birkmeyer |
| 2009/0228053 A1 | 9/2009 | Kolb |
| 2009/0228054 A1 | 9/2009 | Hoffman |
| 2009/0228055 A1 | 9/2009 | Jackson |
| 2009/0240292 A1 | 9/2009 | Butler |
| 2009/0254125 A1 | 10/2009 | Predick |
| 2009/0275994 A1 | 11/2009 | Phan |
| 2009/0306721 A1 | 12/2009 | Kirschman |
| 2010/0004696 A1 | 1/2010 | Jackson |
| 2010/0036434 A1 | 2/2010 | Ely |
| 2010/0057126 A1 | 3/2010 | Hestad |
| 2010/0063552 A1 | 3/2010 | Chin |
| 2010/0121385 A1 | 5/2010 | Blain |
| 2010/0137991 A1 | 6/2010 | Ainsworth |
| 2010/0160921 A1 | 6/2010 | Sun |
| 2010/0238572 A1 | 9/2010 | Tao |
| 2010/0292742 A1 | 11/2010 | Stad |
| 2010/0294595 A1 | 11/2010 | Osburn |
| 2010/0331901 A1 | 12/2010 | Iott |
| 2011/0004222 A1 | 1/2011 | Biedermann |
| 2011/0034961 A1 | 2/2011 | Runco |
| 2011/0040328 A1 | 2/2011 | Miller |
| 2011/0040335 A1 | 2/2011 | Stihl |
| 2011/0077692 A1 | 3/2011 | Jackson |
| 2011/0087293 A1 | 4/2011 | Ferreira |
| 2011/0087298 A1* | 4/2011 | Jones ................. A61B 17/7086 606/86 A |
| 2011/0106187 A1 | 5/2011 | Foley |
| 2011/0137358 A1 | 6/2011 | Manninen |
| 2011/0184469 A1 | 7/2011 | Ballard |
| 2011/0202137 A1 | 8/2011 | Keith |
| 2011/0218583 A1 | 9/2011 | Smith |
| 2011/0234466 A1 | 9/2011 | Yamada |
| 2011/0238117 A1 | 9/2011 | Geist |
| 2011/0257692 A1 | 10/2011 | Sandstrom |
| 2011/0282402 A1 | 11/2011 | Chao |
| 2012/0016425 A1 | 1/2012 | Shaffrey |
| 2012/0078316 A1 | 3/2012 | Anderson |
| 2012/0100497 A1 | 4/2012 | Joo |
| 2012/0123431 A1 | 5/2012 | Robinson |
| 2012/0158070 A1 | 6/2012 | Jackson |
| 2012/0165876 A1 | 6/2012 | Nichols |
| 2012/0191144 A1 | 7/2012 | Peultier |
| 2012/0203288 A1 | 8/2012 | Lange |
| 2012/0271365 A1 | 10/2012 | Daubs |
| 2012/0277800 A1 | 11/2012 | Jackson |
| 2013/0035728 A1 | 2/2013 | Jackson |
| 2013/0035729 A1 | 2/2013 | Hammer |
| 2013/0072987 A1 | 3/2013 | Justis |
| 2013/0090697 A1 | 4/2013 | George |
| 2013/0110124 A1 | 5/2013 | Gleason |
| 2013/0184763 A1 | 7/2013 | McClintock |
| 2013/0296949 A1 | 11/2013 | Sicvol |
| 2013/0296950 A1 | 11/2013 | Landry |
| 2013/0304130 A1 | 11/2013 | Jackson |
| 2014/0031872 A1 | 1/2014 | Jackson |
| 2014/0031873 A1 | 1/2014 | Jackson |
| 2014/0039567 A1 | 2/2014 | Hoefer |
| 2014/0052187 A1* | 2/2014 | McBride ............ A61B 17/7085 606/264 |
| 2014/0058465 A1 | 2/2014 | Nichols |
| 2014/0074106 A1 | 3/2014 | Shin |
| 2014/0100613 A1 | 4/2014 | Iott |
| 2014/0100617 A1 | 4/2014 | Sandstrom |
| 2014/0100618 A1 | 4/2014 | Kolb |
| 2014/0107708 A1 | 4/2014 | Biedermann |
| 2014/0163625 A1 | 6/2014 | Meyer |
| 2014/0194939 A1 | 7/2014 | Seelig |
| 2018/0042645 A1* | 2/2018 | Gunn ............... A61B 17/00234 |

FOREIGN PATENT DOCUMENTS

| | | |
|---|---|---|
| EP | 1839606 | 11/2008 |
| EP | 2324787 A1 | 5/2011 |
| EP | 2070485 | 9/2011 |
| EP | 2462889 A1 | 6/2012 |
| EP | 2574297 A1 | 4/2013 |
| EP | 2719347 A1 | 4/2014 |
| FR | 2920663 A1 | 3/2009 |
| JP | 2003265492 A | 9/2003 |
| WO | WO-02094114 A1 | 11/2002 |
| WO | WO-2012127267 | 9/2012 |
| WO | WO-2012127268 | 9/2012 |

* cited by examiner

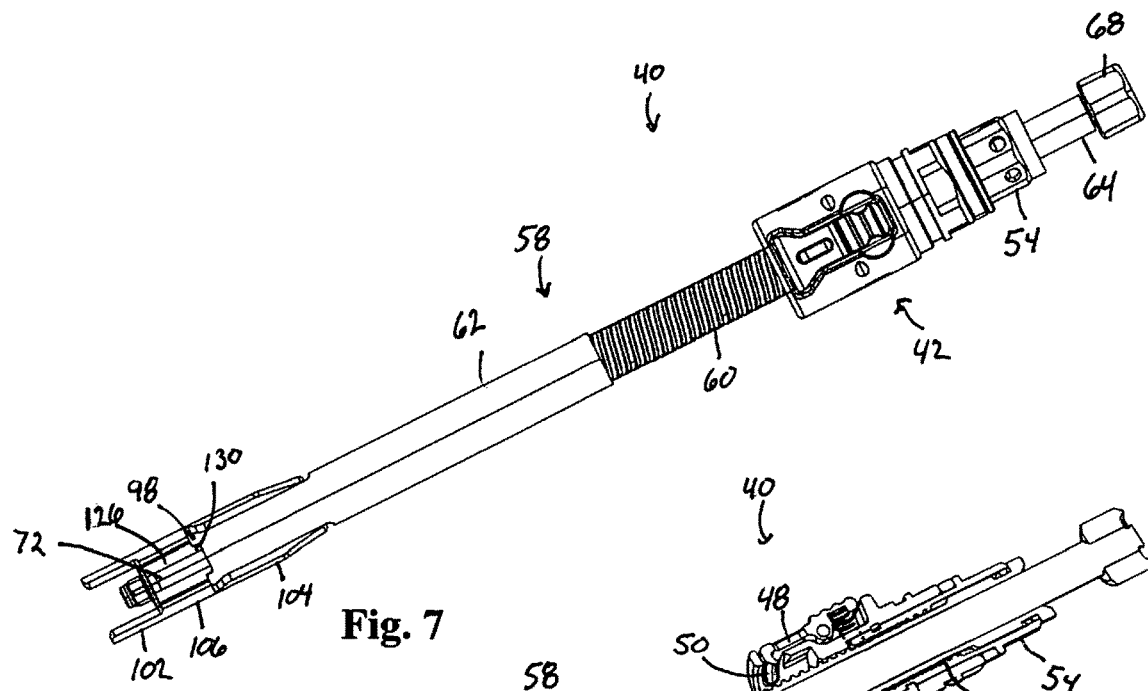
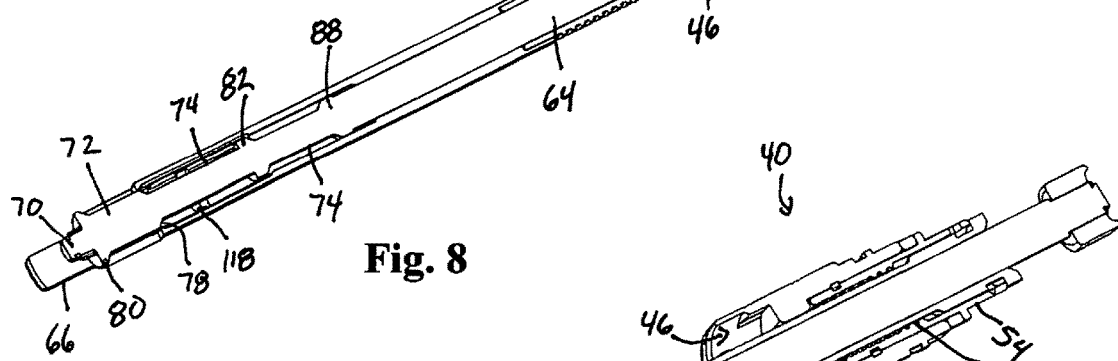
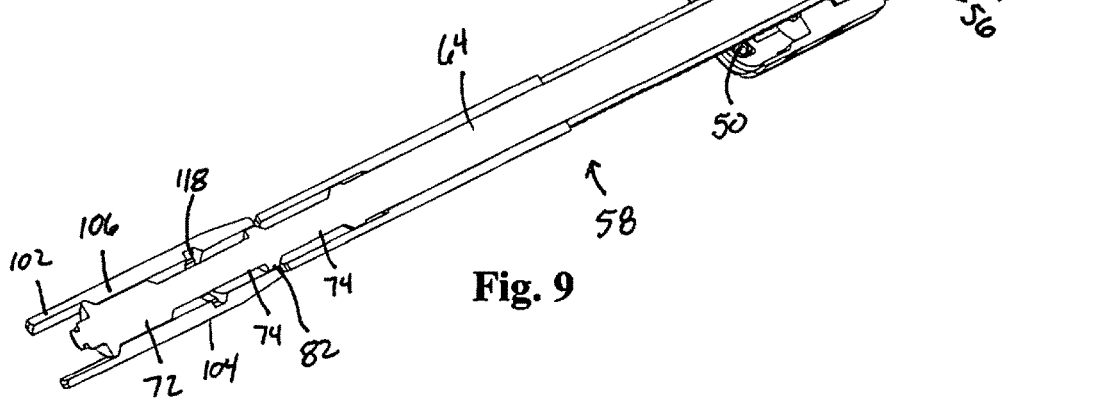

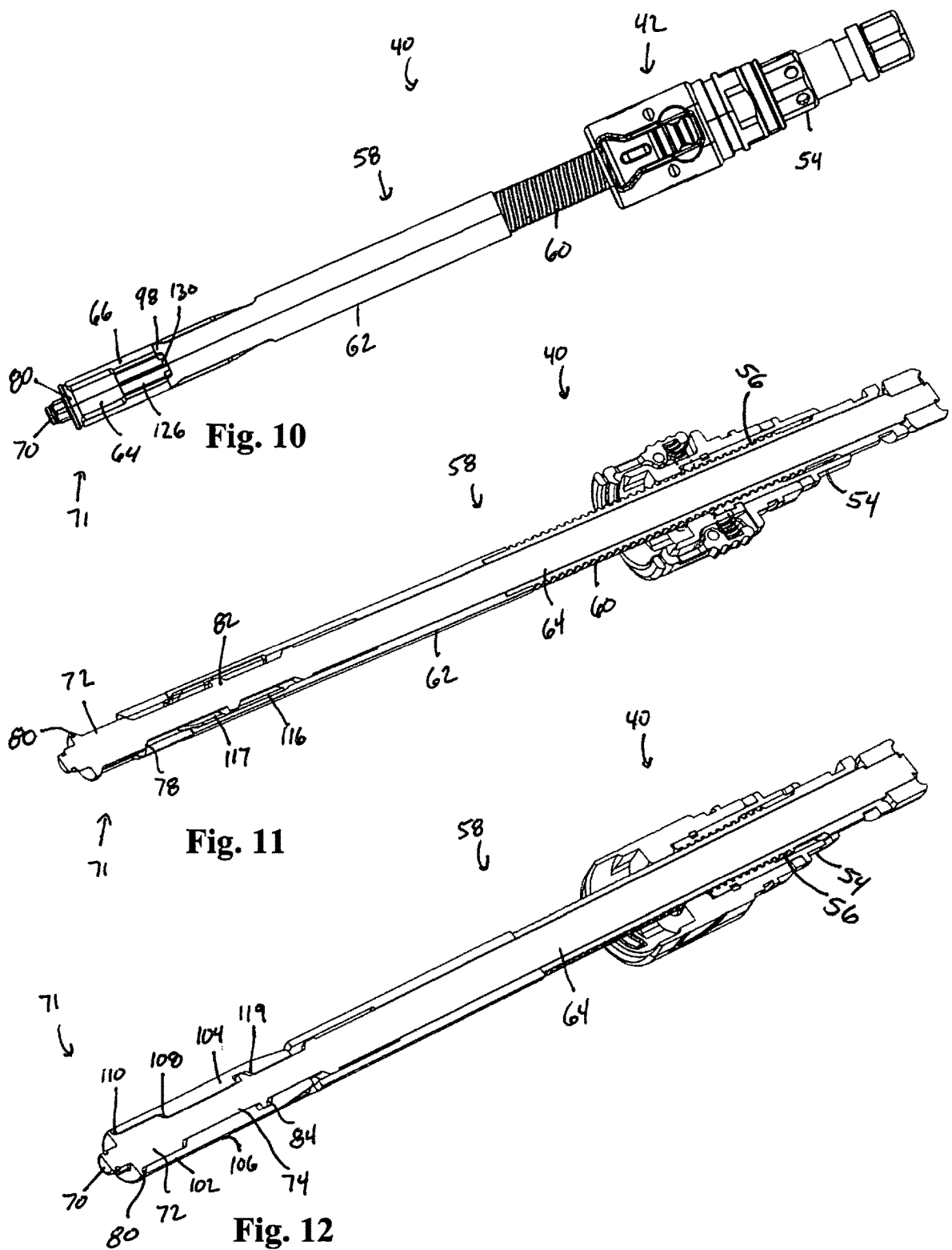

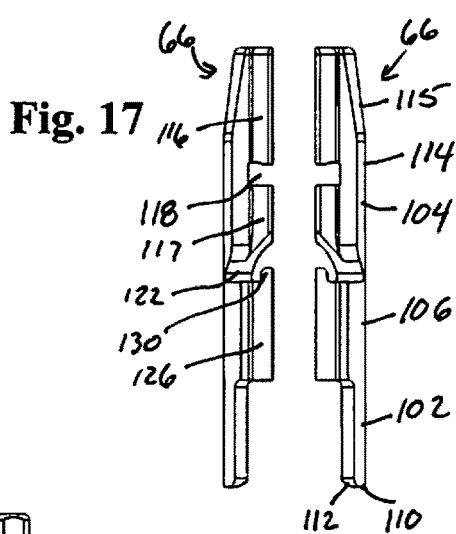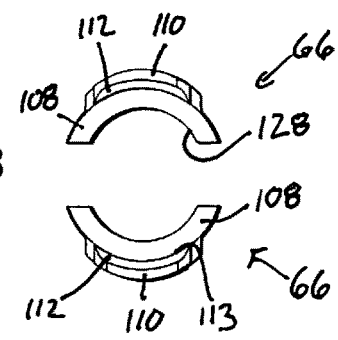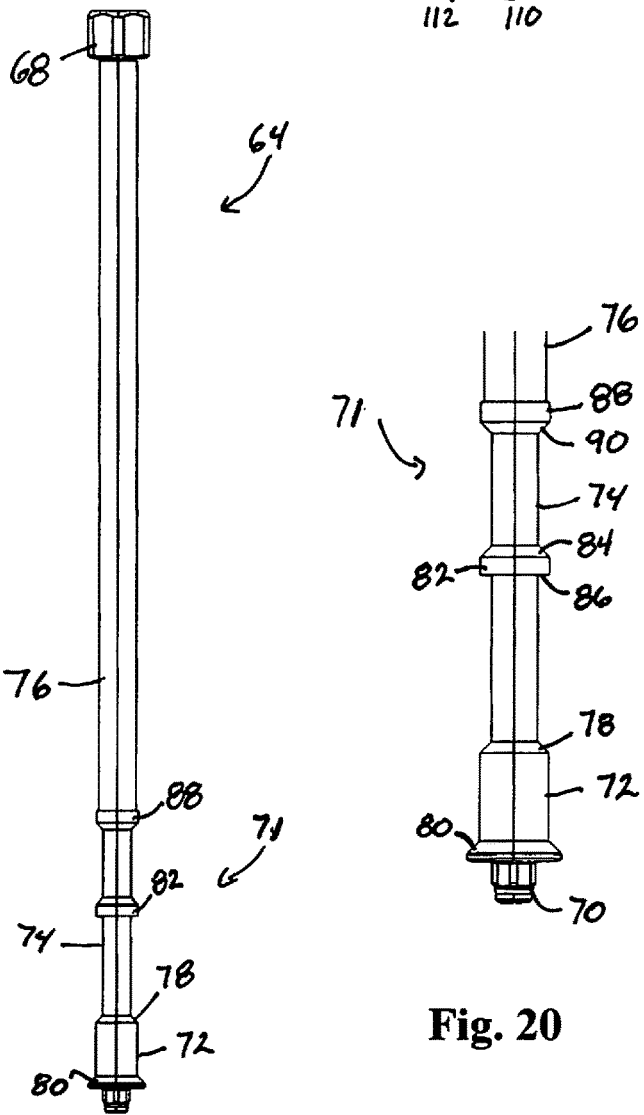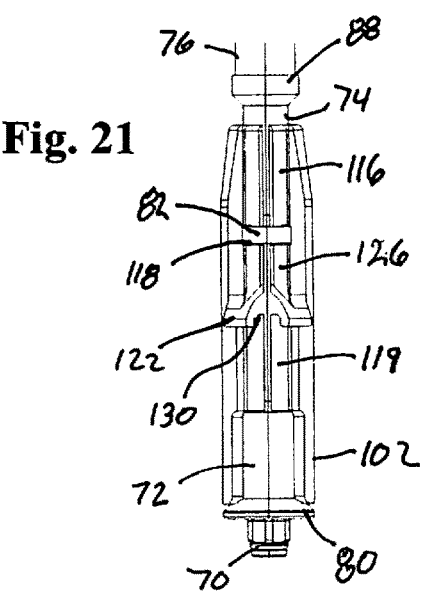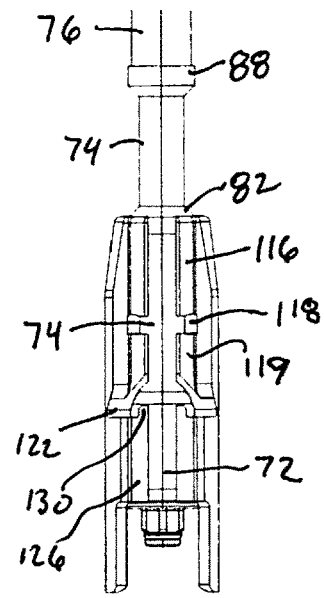
Fig. 17
Fig. 18
Fig. 19
Fig. 20
Fig. 21
Fig. 22

SPINAL FIXATION SYSTEM

CROSS REFERENCE TO RELATED APPLICATIONS

The present application is a continuation of U.S. patent application Ser. No. 16/512,698, filed Jul. 16, 2019; which is a continuation of U.S. patent application Ser. No. 15/829,955, filed Dec. 3, 2017, now U.S. Pat. No. 10,398,481, issued Sep. 3, 2019; which claims the benefit of priority from U.S. Provisional Patent Application Ser. No. 62/403,501, filed on Oct. 3, 2016, the entire contents of which are each hereby expressly incorporated by reference into this disclosure as if set forth in its entirety herein.

FIELD

This application describes surgical instruments for reducing a rod during construction of a minimally invasive fixation construct across one or more segments of the spinal column.

BACKGROUND

Spinal fixation constructs are utilized to provide stability to the spine. Most often the fixation construct is used as an adjunct to fusion surgery during which adjacent vertebrae are prepared to facilitate bone growth between them, thereby eliminating motion between the vertebrae. Because motion between the vertebrae tends to inhibit bone growth, the fixation constructs are employed to prevent motion so that bone can grow and achieve a solid fusion. When the position of one or more vertebrae must be adjusted to restore a more natural alignment of the spinal column, the fixation construct also serves to maintain the new alignment until fusion is achieved. Fixation constructs of various forms are well known in the art. Most commonly, the fixation construct is a plate anchored to the anterior column with multiple bone anchors or a posterior fixation construct including multiple anchors and a connecting rod anchored to the posterior elements of the spine. For a posterior fixation construct the anchors (typically pedicle screws) are anchored into the pedicles of each vertebra of the target motion segment. The anchors are then connected by a fixation rod that is locked to each anchor, thus eliminating motion between the adjacent vertebrae of the motion segment. The posterior fixation construct may be applied unilaterally or bilaterally. Additionally the posterior fixation construct may be applied across multiple levels or motion segments.

The fixation anchors utilized in posterior fixation constructs generally include an anchor portion and a rod housing. The rod housing includes a pair of upstanding arms separated by a rod channel in which the fixation rod is captured and locked. When constructing the posterior fixation construct the surgeon must align and seat the rod in the rod channel. This can be a challenge, particularly when one or more of the vertebrae to be connected is out of alignment leaving the associated anchor offset vertically and/or horizontally from the remaining anchor(s) of the construct. Constructing the posterior fixation construct under minimally invasive access conditions (e g minimizing overall incision length and muscle stripping as compared to traditional open procedures) also increases the difficulty of aligning the rod with the rod channel of the anchor.

Rod reducers are often used to facilitate alignment and seating of the rod in the anchor housing. Rod reducers often work by engaging the anchor housing with a first portion and then driving the rod towards the housing and/or pulling the housing towards the rod with a second portion that moves relative to the first portion. With minimally invasive systems the reducer may attach to a guide assembly which is itself attached to the anchor. Generally, reducers employed with minimally invasive systems must have a portion that passes over and translates along the outside of the guide to engage the rod, or, pass directly through the center of the guide. While both of these configurations may be effective, there are disadvantages. For example, passing a reducer over the outside of the guide requires increasing the incision size in order to fit the reducer. On the other hand, passing the reducer through the center of the guide provides for one point of contact on the rod, in the middle of the anchor housing, which leaves a potential for the rod not to align fully with the housing. The instruments, tools, and techniques described herein are directed towards reducing these challenges and others associated with posterior spinal fixation.

BRIEF DESCRIPTION OF THE DRAWINGS

Many advantages of the present invention will be apparent to those skilled in the art with a reading of this specification in conjunction with the attached drawings:

FIG. 7 is another perspective view of the reduction instrument shown in FIG. 3;

FIG. 8 is a cross section of the reduction instrument shown in FIG. 7;

FIG. 9 is another cross section of the reduction instrument shown in FIG. 7;

FIG. 10 is another perspective view of the reduction instrument shown in FIG. 4;

FIG. 11 is a cross section of the reduction instrument shown in FIG. 10;

FIG. 12 is another cross section of the reduction instrument shown in FIG. 10;

FIG. 17 is a side view of the pair of reduction legs of the reduction instrument of FIG. 3 in isolation;

FIG. 18 is a distal (bottom) view of the pair of reduction legs of FIG. 17;

FIG. 19 is a side view of a central shaft of the reduction instrument of FIG. 3 in isolation;

FIG. 20 is a close up side view of the distal end of the central shaft of FIG. 19;

FIG. 21 is a close up side view of the distal end of the central shaft and reduction legs in the contracted position;

FIG. 22 is a close up side view of the distal end of the central shaft and reduction legs in the deployed or extended position;

DETAILED DESCRIPTION

Figure 1:
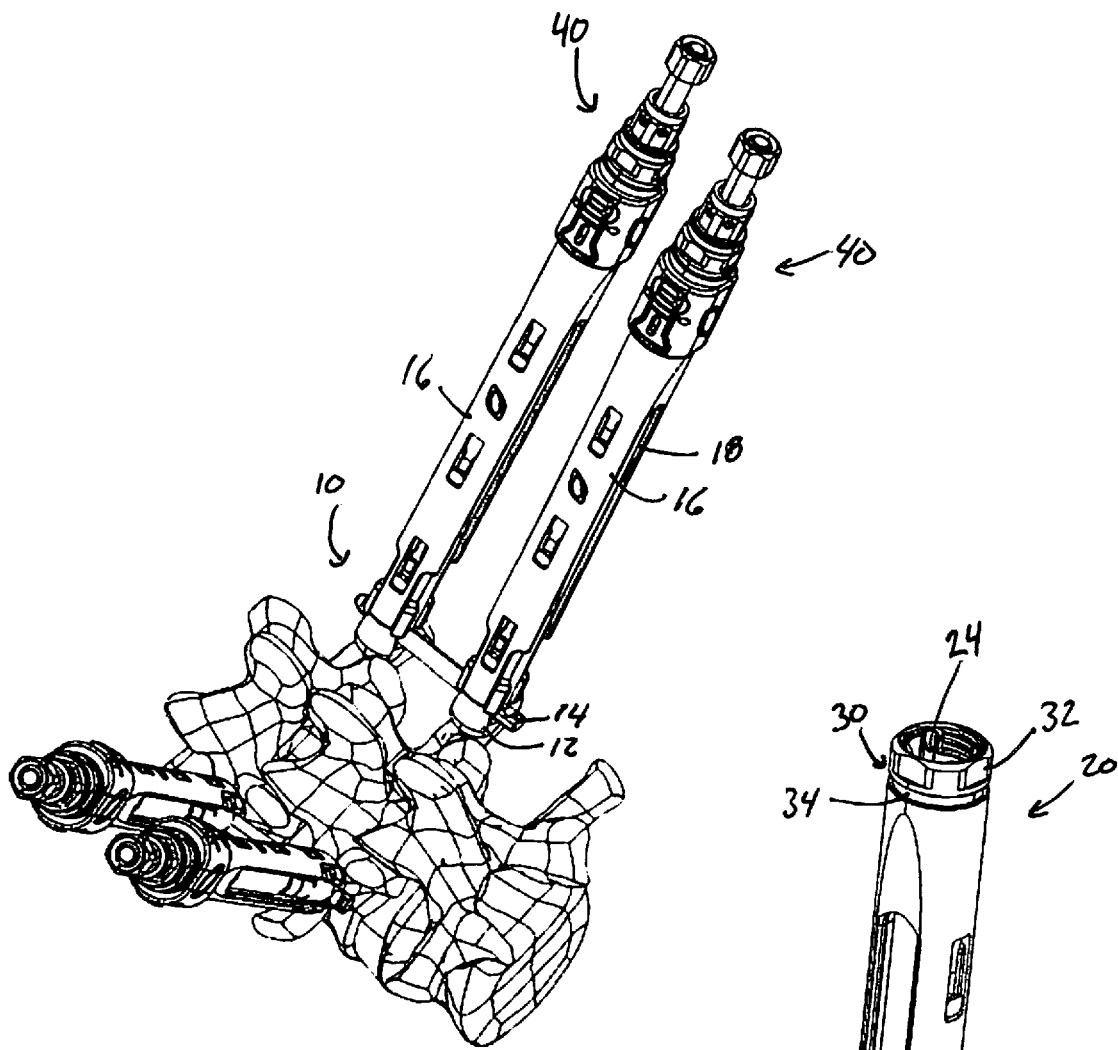
FIG. 1 is a perspective view of a lumbar spine illustrating the minimally invasive implantation of a spinal fixation construct, according to one example embodiment.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

The terms "first," "second" and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The terms "proximal" and "distal" as used herein are relative to a user of the disclosed systems and devices. More specifically, when the spinal fixation system or components thereof are in use on a patient, the proximal direction is the direction toward the user (surgeon), and the distal direction is the direction toward the patient. In the context of the disclosed devices, the proximal and distal directions are directions along the axis of the generally cylindrical guide assemblies, pedicle screws, reduction instruments, etc. disclosed.

The term "axial" refers to the dimension of the generally cylindrical guide assemblies, pedicle screws, reduction instruments, etc. disclosed as defined by the axis of such a cylinder. A structure that is axial extends in the distal and proximal directions.

The term "radial" refers to the dimension of the generally cylindrical guide assemblies, pedicle screws, reduction instruments, etc. disclosed as defined by a radial vector of such a cylinder. A structure that is radial extends toward and away from the axis of such a structure.

The term "circumferential" refers to a dimension or direction defined by the circumference of any of generally cylindrical guide assemblies, pedicle screws, reduction instruments, etc. disclosed. A structure that is circumferential will thus be generally arcuate in shape.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fixation system disclosed herein boasts a variety of inventive features and components that warrant patent protection, both individually and in combination.

FIG. 1 illustrates the minimally invasive implantation of a spinal fixation construct 10 across one or more levels of a spine. The fixation construct 10 includes bone anchors 12 connected by a fixation rod 14. Guide assemblies (or "guides") 16 are used to implant the fixation construct 10 under minimally invasive conditions. That is, the overall length of skin incisions required to install the fixation construct may be minimized compared to traditionally open pedicle screw procedures. For example, the guides 16 extend proximally out of the patient when the anchor 12 is engaged to the spine and a rod channel 18 through the guide 16 helps direct the rod 14 into the proper position connecting the bone anchors 12 without requiring the extended incisions needed to fully expose the spinal segments to be fixated. A variety of instruments may be configured to work with the guides to further facilitate the installation and assembly of the spinal fixation construct, including by way of example rod reduction instruments, such as the reduction instrument shown in FIGS. 3-28, as well as rod inserters, compression instruments, lock screw inserters, guide adjusters, tap guides, and dilators. The construct shown being implanted in FIG. 1 is a single level, bi-lateral construct, but, the implants and tools described herein may be used as part of unilateral constructs and/or across multiple spinal levels.

Figure 2:
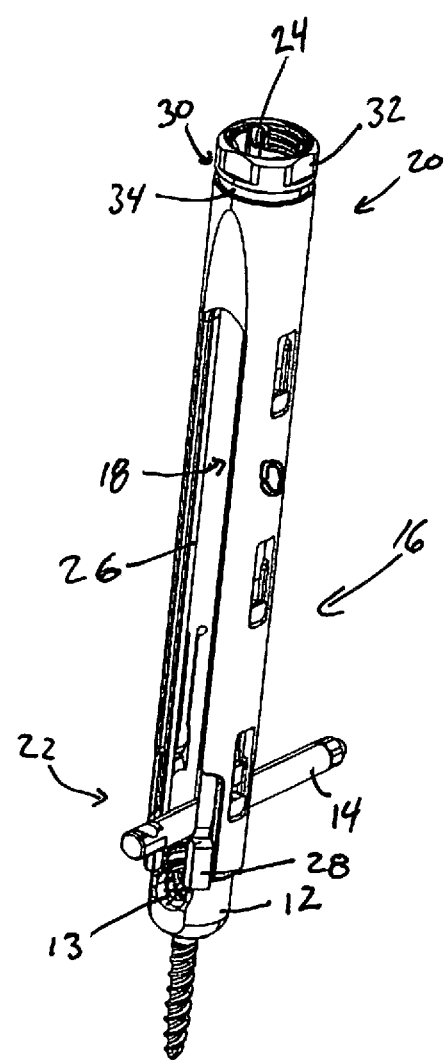
FIG. 2 is a perspective view of an example guide assembly used during the minimally invasive implantation of a bone anchor and fixation rod of the fixation construct shown in FIG. 1.

FIG. 2 depicts one example embodiment of the guide 16 that facilitates implantation of the fixation construct minimally invasively. The guide 16 and bone anchor 12 are of the type shown and described in U.S. patent application Ser. No. 13/456,210, filed Apr. 25, 2012 (now U.S. Pat. No. 9,198,698), and U.S. patent application Ser. No. 14/631,839, filed Feb. 25, 2015, the entire contents of which are each expressly incorporated by reference herein. The guide 16 includes a proximal end 20, a distal end 22, and a central passage 24 extending from the proximal end 20 to the distal end 22. A pair of opposed rod slots 26 opening to the distal end 22 and extending proximally for a length along the guide 16 and in communication with the central passage 24 to form the rod channel 18 for guiding the rod into connection with the bone anchor 12. The distal end 22 includes an engagement feature(s) 28 that detachably couples the guide 16 and anchor 12. When the guide and anchor are coupled the rod channel 18 aligns and communicates with a rod channel 13 in the bone anchor 12 that seats the rod 14. The proximal end includes an engagement feature(s) 30 that may detachably couple the guide 16 with one or more instruments used in cooperation with the guide to implant the construct. In the illustrated embodiment the engagement feature includes a keyed end 32 and an attachment groove 34.

Figures 3, 4:
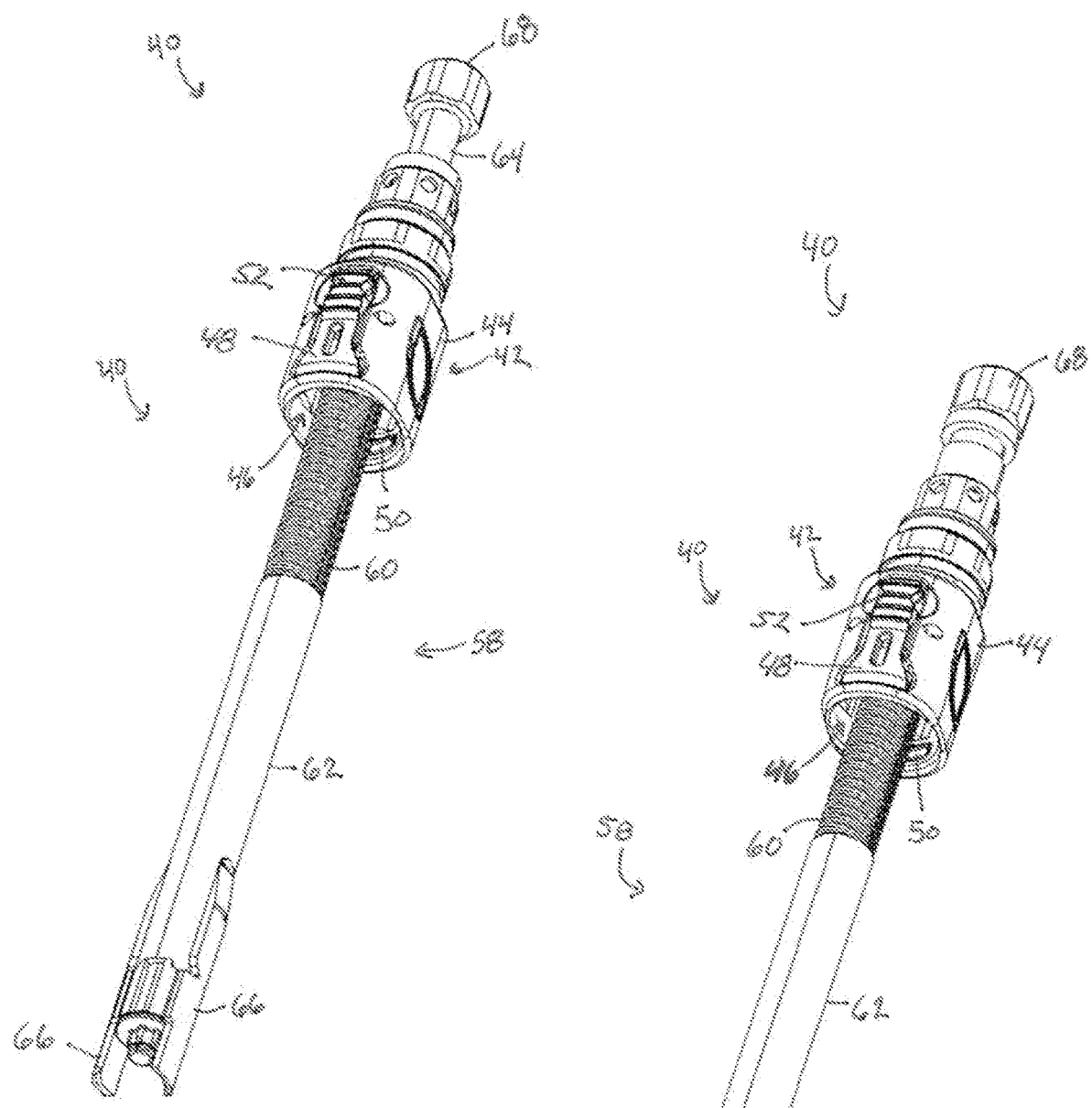
FIG. 3 is a perspective view of an example embodiment of a rod reduction instrument with reduction legs deployed to facilitate rod reduction during implantation of the spinal fixation construct of FIG. 1.
FIG. 4 is a perspective view of the embodiment of the reduction instrument shown in FIG. 3 with the reduction legs contracted.
Figure 5:
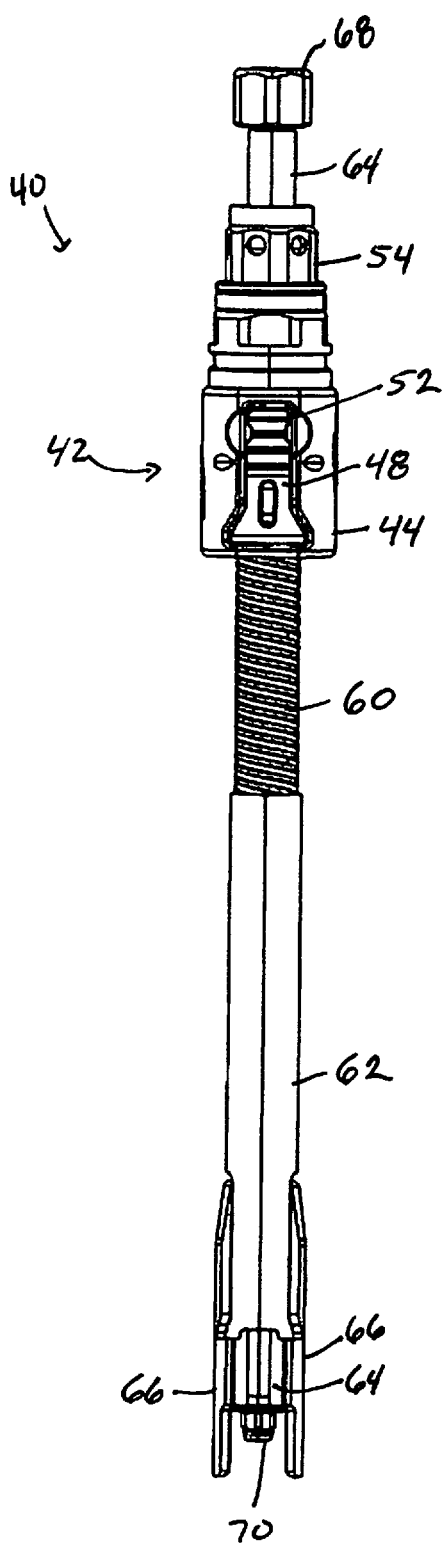
FIG. 5 is a front view of the reduction instrument shown in FIG. 3.
Figure 6:
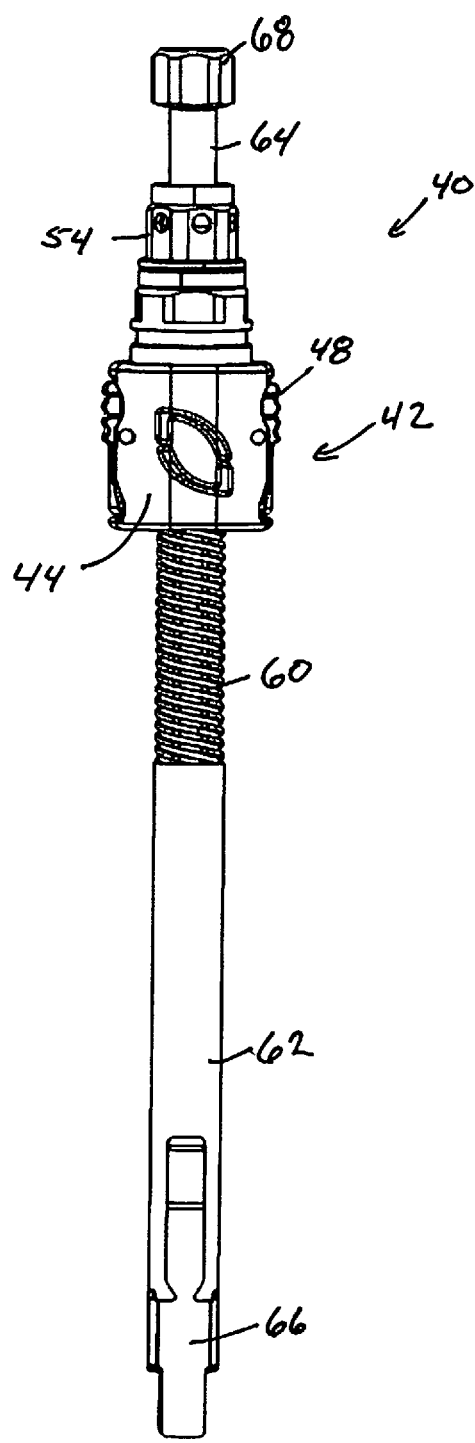
FIG. 6 is a side view of the reduction instrument shown in FIG. 3.
Figure 13:
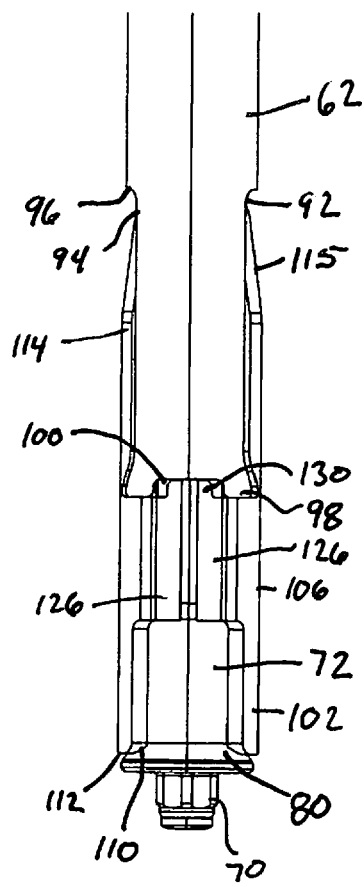
FIG. 13 is a close-up of the distal end of the reduction instrument of FIG. 3, illustrating the central shaft, extension legs, and lower shaft when the reduction legs are in the contracted position.
Figure 14:
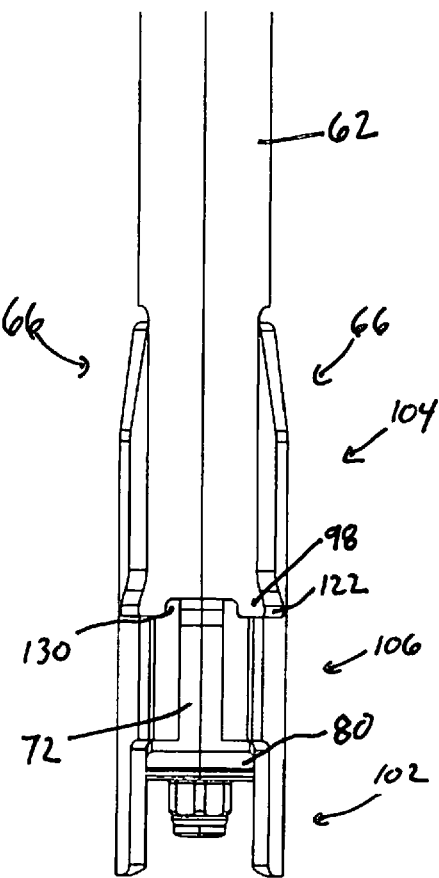
FIG. 14 is a close-up of the distal end of the reduction instrument of FIG. 3, illustrating the central shaft, extension legs, and lower shaft when the reduction legs are in the deployed position.
Figure 15:
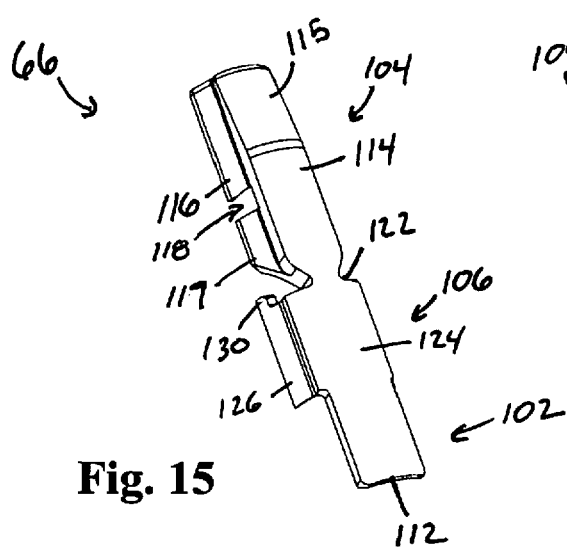
FIG. 15 is a perspective view of an exterior side of one of the reduction legs of the reduction instrument of FIG. 3 in isolation.
Figure 16:
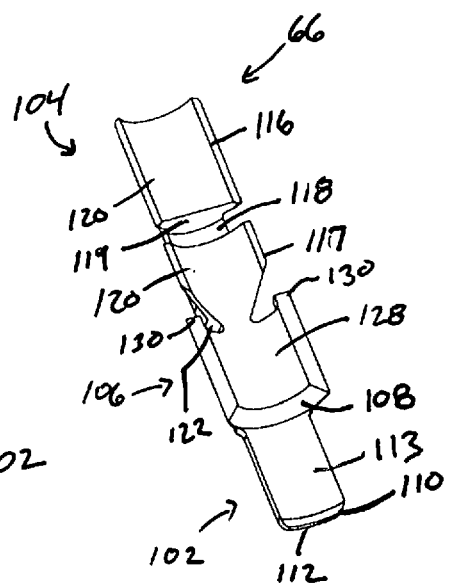
FIG. 16 is a perspective view of an interior side of the reduction leg of FIG. 15.

FIGS. 3-28 illustrate an embodiment of a reduction instrument (or "reducer") 40 that may be used during the implantation of the spinal fixation construct 10 to draw the rod 14 and bone anchor together. That is, the reduction instrument is used (when necessary) to forcibly seat ("reduce") the spinal rod 14 into the bone anchor 12. The reducer 40 can also deliver a lock screw (not shown) to the anchor to the secure the rod and maintain the reduction. As illustrated in FIGS. 3-4, the reducer 40 is configured to transition between a contracted or insertion arrangement (FIG. 4), in which reduction legs 66 are in a contracted position and have an effective diameter that approximates the remainder of the reduction shaft such that the reducer may be inserted through the central passage of the guide 16, and an expanded or reduction arrangement (FIG. 3) in which the reduction legs extend distally and expand outward to increase the effective diameter, providing two points of contact on the rod (one at each end of the bone anchor rod channel 13).

With reference to FIGS. 3-12, the reduction instrument includes a connector 42 that releasably couples the reduction instrument 40 to the guide assembly 16 (via the engagement feature 30). The connector 42 has a connector body 44 containing a guide cavity 46 into which the engagement feature 30 of the guide assembly 16 is received. The keyed end 32 is keyed to the guide cavity 46 so as to prevent rotation of the guide assembly 16 relative to the connector body 42. Spring locks 48 on the connector body 44 engage the attachment groove 34 to prevent translation of the guide assembly 16 relative to the connector body 44. Specifically, the spring locks 48 include ridges 50 that extend through the connector into the guide cavity 46 and engage the groove 34. Tapered surfaces on the ridges allow the proximal end 20 of the guide assembly 16 to push past the spring locks 48 until the ridges snap into place within the circumferential groove 34. To release the connection between the reducer 40 and the guide assembly 16, the proximal ends of the spring locks 48 can be depressed causing the ridges to disengage from the groove 34, thus allowing the removal of the connector 40 from the guide 16. The proximal end of the connector 42 includes a reduction grip 54 that is freely rotatable but translationally fixed to the connector body 44. Interior threads 56 are situated around the interior surface of the second grip 54.

In addition to the connector 42, the reducer 40 has a reduction shaft 58 and a central shaft 64. The reduction shaft 58 includes an upper shaft 60 with exterior threading, a lower shaft 62, and a pair of reduction legs 66. The exterior threads on the upper shaft 60 mate with the interior threading 56 of the reduction grip 54 such that rotation of the reduction grip causes the upper shaft 60 to translate up or down through the connector 42. The lower shaft 62 is coupled to the upper shaft 60 and translates with it. Likewise, the reduction legs 66 are coupled to the lower shaft 62 and also translates with the upper shaft 60.

As best viewed in FIGS. 8, 9, 11 and 12, the central shaft 64 extends axially through the entire length of upper and lower shafts 60, 62. The central shaft 64 has a first rotation grip 68 fixed at a proximal end of the shaft. At the distal end of the central shaft 64 is a lock screw interface 70. The lock screw interface is configured to engage and hold a lock screw at the distal end of the reducer while reduction is applied, and thereafter engage the lock screw to the bone anchor 12 before relieving the reduction force. Such engagement may be facilitated by a lock screw engagement feature, such as a hexalobe protrusion. The engagement feature may be dimensioned for a friction fit with a complementary engagement feature in the lock screw in order to maintain the lock screw on the interface, or alternatively, other holding features (e.g. spring rings, ball detents, etc.) may be used to maintain the lock screw on the interface during use. To deliver the lock screw, the grip 68 can be manipulated to rotate the central shaft about its axis and to translate the central shaft in the proximal and distal directions through the upper and lower shafts 60, 62.

The central shaft 64 further includes a functional distal end 71, illustrated best in FIG. 19-20 (depicting the central shaft alone), that interacts with the reduction legs 66 to increase or decrease the effective diameter of the reduction legs. The functional distal end 71 has a lower portion 72 with a diameter that generally matches the diameter of the proximal end 76 of the center shaft 54, and an upper portion 74. The upper portion 74 separates the lower portion 72 of the distal end 70 from the proximal end 76 and has a smaller diameter relative to the lower portion 72. The lower portion 72 includes a first flare or taper 78 facing proximally and connecting the lower portion 72 to the upper portion 74. The lower portion 72 includes a second flare 80 with a proximally facing taper that separates the lower portion from the lock screw interface 70. A first shoulder 82 having a proximal tapered surface 84 and a straight distal surface 86 is situated near the middle of the upper portion 74 and a second shoulder 88 having a tapered distal surface 90 separates the upper portion from the proximal end 76.

Figure 23:
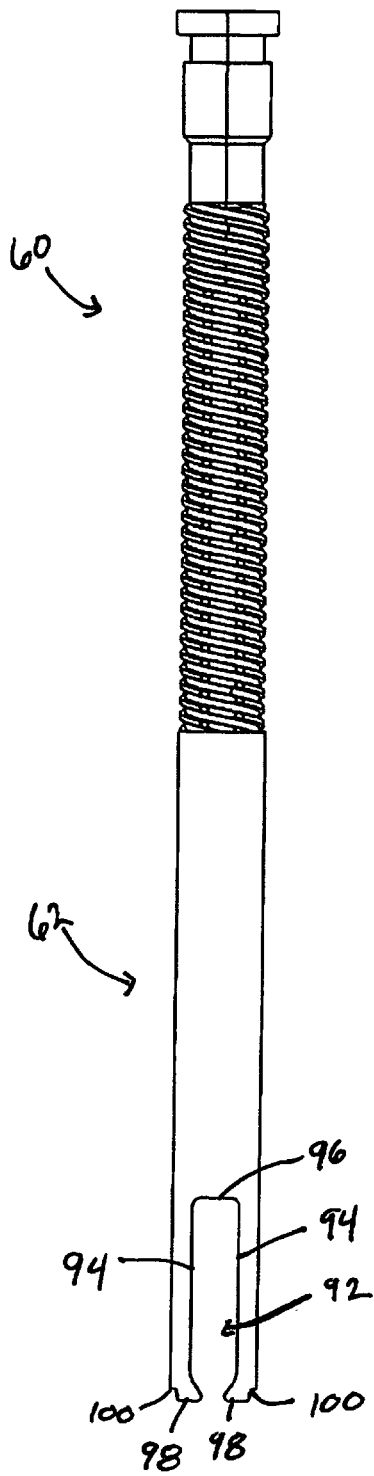
FIG. 23 is a side view of the lower shaft of the reduction instrument in FIG. 3.
Figure 24:
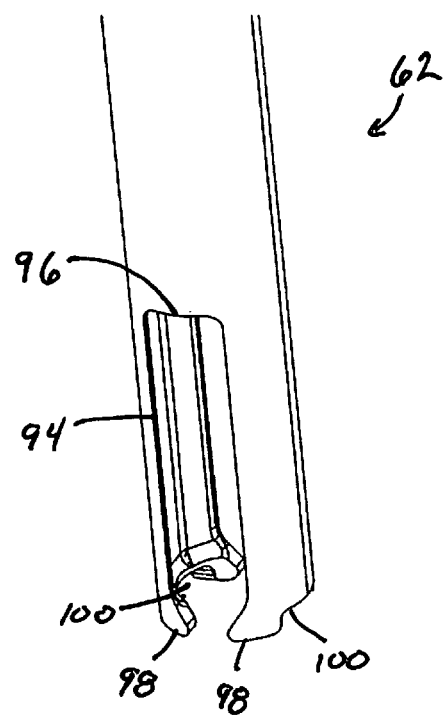
FIG. 24 is a perspective view of the distal end of the lower shaft of FIG. 23
Figures 25, 26:
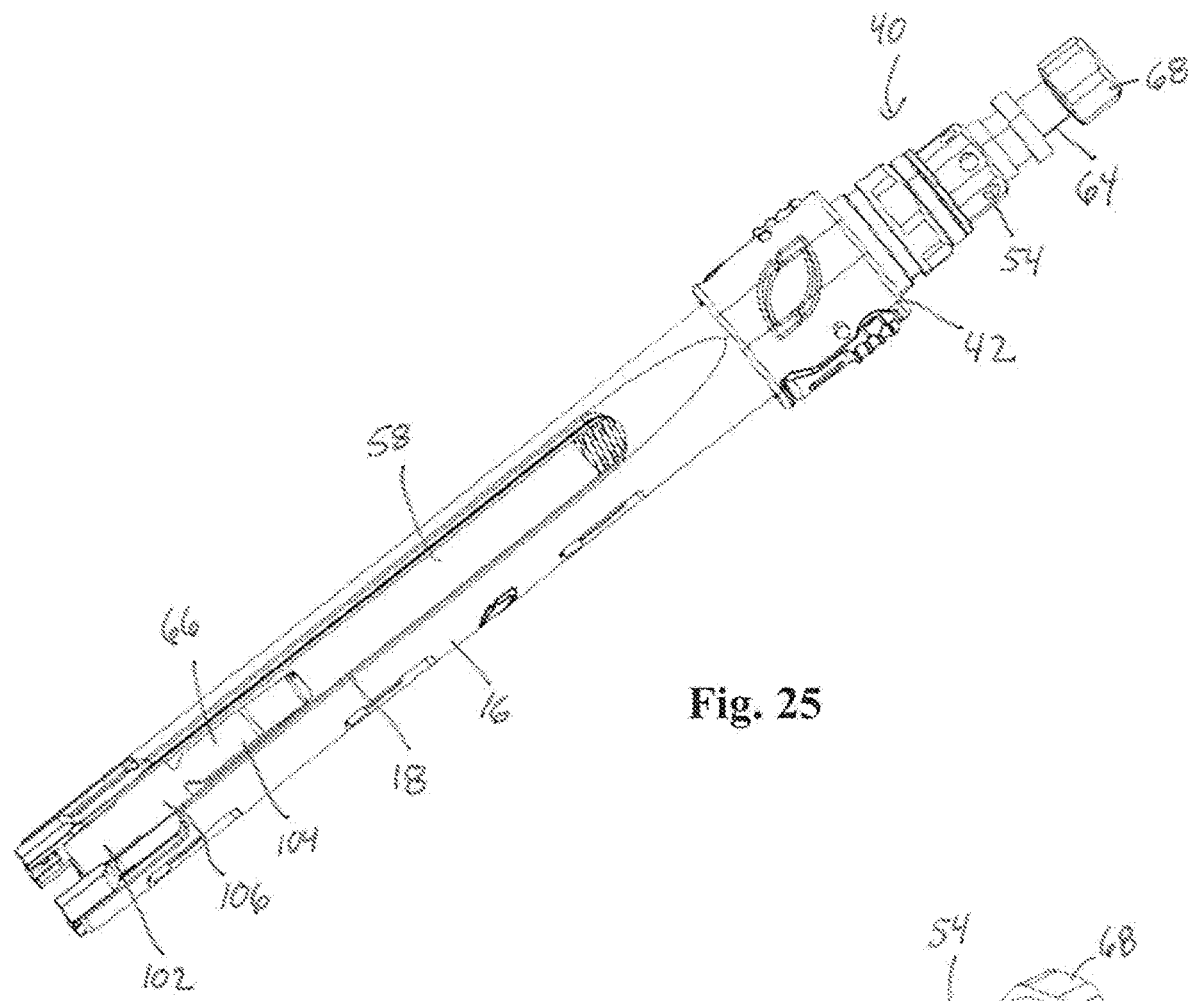
FIG. 25 is a perspective view of the reduction instrument of FIG. 3 deployed through the guide assembly of FIG. 2.
FIG. 26 depicts the guide assembly and reduction instrument of FIG. 25 with a cross section proximate the distal end to reveal the positions of the central shaft, reduction legs, lower shaft, and guide assembly when the reduction legs are in the expanded position.
Figure 27:
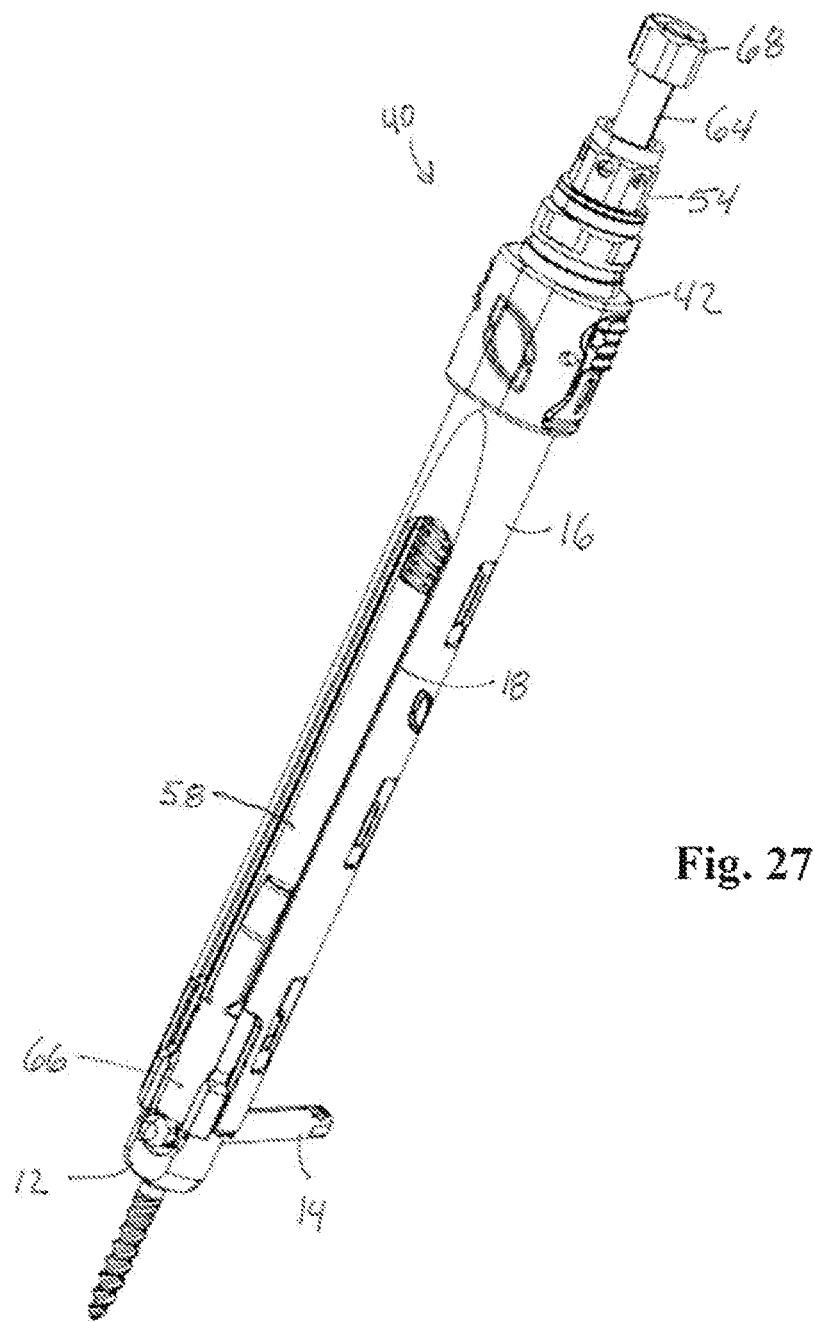
FIG. 27 is a perspective view of the reduction instrument of FIG. 3 deployed through the guide assembly of FIG. 2 to reduce a rod into an anchor coupled to the guide assembly.
Figure 28:
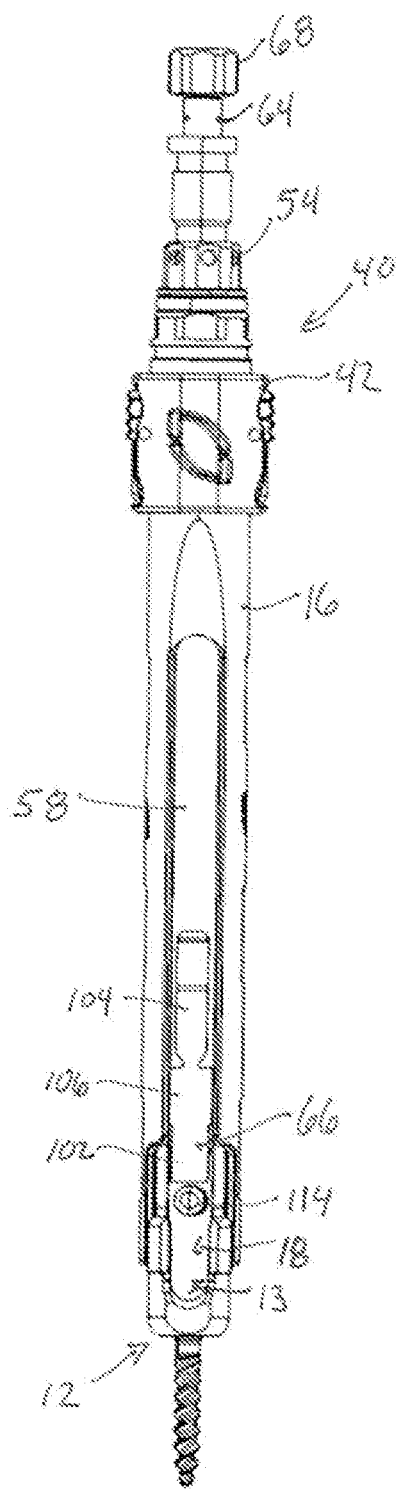
FIG. 28 is a side view of the reduction instrument and guide assembly of FIG. 27 prior to reduction of the rod.
Figure 29:
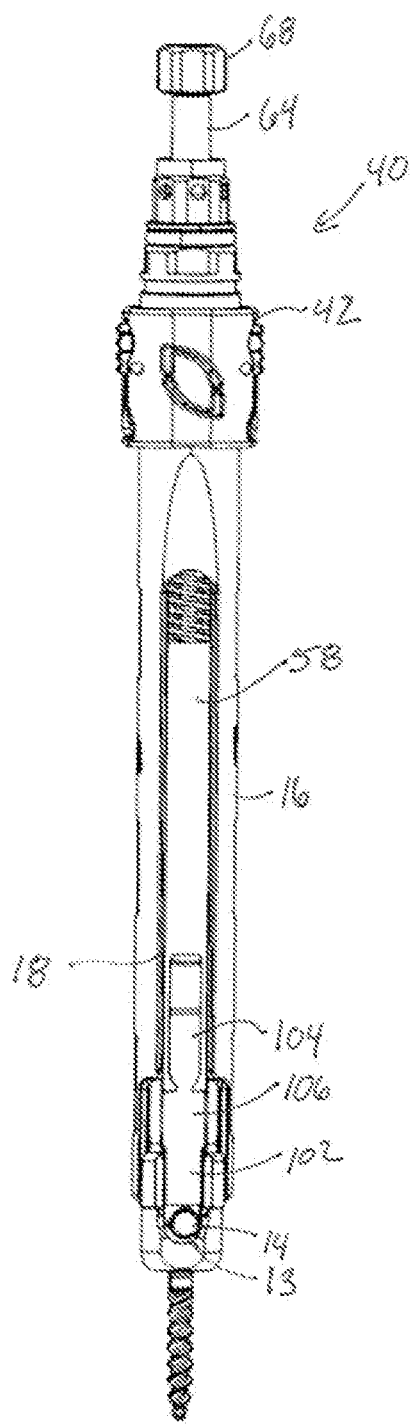
FIG. 29 is a side view of the reduction instrument and guide assembly of FIG. 27 after reduction of the rod.
Figures 30, 31:
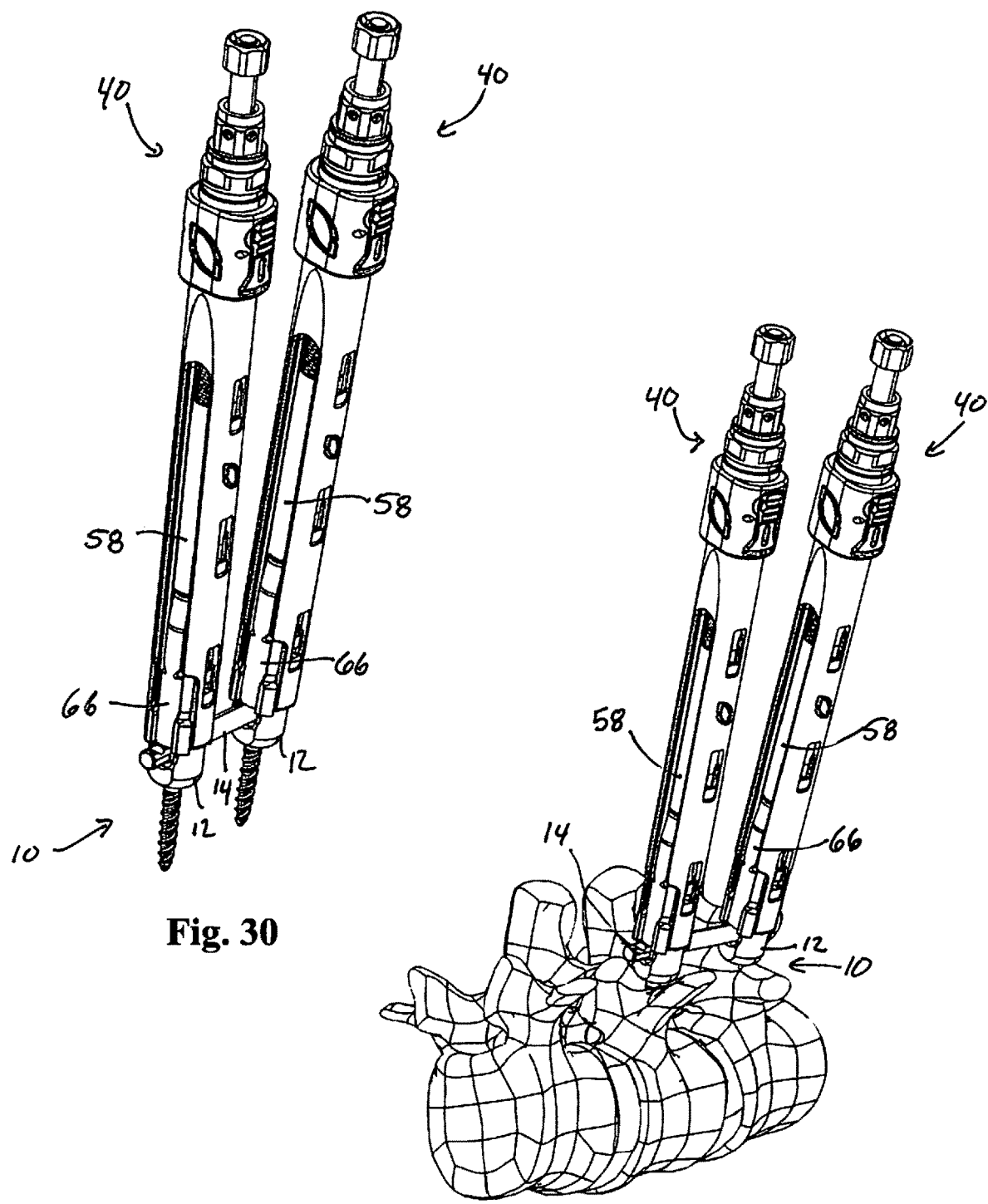
FIG. 30 depicts a pair of reduction instruments deployed through a pair of guide assemblies, respectively, to reduce a rod into a pair of anchors coupled to the guide assemblies to assemble the spinal fixation construct.
FIG. 31 shows the spinal fixation construct of FIG. 30 being assembled in a pair of vertebrae of the lumbar spine.

With reference to FIGS. 23-24, the lower shaft 62 of the reduction shaft 54 is described in further detail. The lower shaft 62 is coupled to the upper shaft 60 at its proximal end and two translate together as the reduction grip 54 rotates around the threading of the upper shaft. The lower shaft 62 comprises a pair of axial cutout portions 92, through which the reduction legs 66 extend radially when in the expanded position. In the exemplary embodiment shown, each axial cutout portion has an axial length that exceeds its circumferential width. Each cutout has two parallel axial sides 94 that are generally parallel to the axis of the lower shaft and which terminate at a circumferential side 96 on their proximal ends. According to the example shown, the axial sides 94 meet the circumferential side 96 at rounded corners. Opposite the circumferential side, the axial sides open through the end of the shaft and have partially converging ends 98. A side recess 100 extends between the converging ends 98 on each side of the axial cutout 92.

The reduction legs 66 are shown in detail in FIGS. 15-18. In the example embodiment illustrated, the reduction leg 66 has a distal portion 102, a proximal portion 104, and an intermediate portion 106. The distal portion 102 has an concave inner surface 113 and a length that is approximately the same as the length of the lower portion 72 of the central shaft 64 such that a first tapered surface 108 at the distal end of the intermediate portion 106 and a second tapered surface 110 at the distal end of the distal portion 102 align with the first and second flares 78, 80 of the central shaft 64 when the reduction legs 66 are in the contracted starting position. In the expanded or extended position, the distal portion 102 extends past the central shaft lock screw interface 70 to engage the fixation rod 14 with rod contact surfaces 112. The proximal portion 104 has a proximal body 114 that is dimensioned to fit within the axial cutout 92. A portion of the body 114 adjacent the proximal end has a tapered outer surface 115. A proximal wing extends from each side of the body 114 and forms a concave proximal inner surface 120 opposite the proximal body 114. A trough 118 dimensioned to receive the first shoulder 82 and having a tapered upper surface 119 interrupts the proximal wing, forming an upper proximal wing 116 and a lower proximal wing 117. The lower proximal wing 117 and proximal body taper inward to a narrow junction with the intermediate portion 106, forming notches 122 that complement and receive the converging ends 98 of the lower shaft 62 to help maintain a translational link between the reduction legs 66 and the lower shaft 62. The intermediate potion 106 has an intermediate body 124 with a width that is too great to fit within the axial cutout 92. An intermediate wing 126 extends from each side of the body 124 and forms a concave intermediate inner surface 128. A projection 130 extends proximally from the end of the intermediate wing 126 on each side. Each projection 130 sits within one of the side recesses 100 of the lower shaft 62 along with one of the projections from the opposing reduction leg.

The reducer 40 is illustrated in the collapsed arrangement in FIGS. 10-13. FIG. 21 also depicts the collapsed configuration with the lower shaft 6 removed for illustrative purposes. The reduction legs 66 are coupled to the lower shaft 62 with the proximal body 114 situated in the axial cutout 92. Converging ends 98 of the lower shaft 62 are situated in the notches 122 of the reduction legs 66 and the projections 130 of the reduction legs are situated in the side recesses 100 to translationally link the reduction legs to the lower shaft. The upper and lower proximal wings 116, 117 are retained within the lower shaft 62 adjacent the axial cutouts 92 for additional stability. The central shaft 64 is fully extended proximally relative to the reduction shaft 58. In this position the distal portion 102 of the reduction leg 66 is aligned with the lower portion 72 of the central shaft distal end 71 such that the distal inner surface 113 is generally flush against lower portion. The intermediate portion 104 and proximal portion 106 are aligned with the narrower upper portion 74 of the central shaft distal end such that the proximal inner surface 120 and intermediate inner surface 128 are generally flush against the upper portion 74. The first tapered surface 108 and second tapered surface 110 match up with the first and second flares 78, 80, respectively, and the first shoulder 82 is situated within the troughs 118 between the upper and lower proximal wings 116, 117. With the reduction legs 66 tucked in in this arrangement, the distance between the outside surfaces of the opposing reduction legs 66 (i.e. the effective diameter of the reduction legs) is approximately the same as the diameter of the reduction shaft 58.

With reference now to FIGS. 7-9, 14, and 22 the reducer 40 is illustrated in the expanded arrangement. Once the reduction shaft has been advanced through the guide 16 and locked in place with the connector 42, the rod slots 26 along the guide provide freedom for the reduction legs 66 (which are aligned with the rod slots when the reducer is properly connected) to expand (see FIGS. 25-27). Expansion of the reduction legs 66 is accomplished by translating the central shaft 64 proximally relative to the reduction shaft 58. This can be done simply by pulling the rotation grip 68 upwards. Alternatively, one will appreciate that rotating the reduction grip 68 to translate the reduction shaft 58 distally while the central shaft is engaged against the rod 14 (e.g. by way of the attached set screw) will also in effect translate the central shaft proximally relative to the reduction shaft. When the central shaft 64 moves proximally, the first flare 78, second flare 80, and first shoulder tapered surface 84 act against the first taper 108, second taper 110, and trough upper surface taper 119, respectively, to force the reduction legs 66 outward away from a longitudinal axis of the central shaft 64. Projections 130 situated in the side recesses 100 of the reductions shaft act as a stop to prevent over expansion of the legs and to provide stability. The distal portion 112 extends past the central shaft distal end. The intermediate portion 106 aligns with the lower portion 72 of the central shaft distal end 71 such that the intermediate portion inner surface 128 is generally flush against lower portion, and the first shoulder 82 is generally flush against the proximal portion inner surface 120, to maintain the reduction legs in the expanded arrangement. In this arrangement the effective diameter of the reduction legs is greater than the diameter of the reduction shaft and provides for contact on the rod 14 at both ends of the bone anchor rod channel 13, reducing the possibility that the rod 14 will not fully seat flush in the rod channel.

Referring to FIGS. 28-31, use of the reducer 40 to facilitate minimally invasive construction of a fixation construct 10 using minimally invasive guide assemblies 16 is described, according to one example. The bone anchors 12 (e.g. pedicle screws) are implanted into the targeted vertebrae with the guide assemblies 16 attached and the fixation rod 14 is introduced through the guide channel 18. A lock screw is attached to the lock screw interface 70 of each reducer 40 to be used. With the reduction legs 66 in the contracted arrangement the reduction shaft 58 is advanced through the central passage 24 of the guide assembly 16 until the engagement feature 30 on the proximal end of the guide is received and locked in the keyed guide cavity 46, fixing the position of the guide 16 and anchor 12 relative to the connector 42. With the reduction legs 66 advanced past the proximal end of the guide and aligned with the rod channel 18, the reducer can be reconfigured into the expanded position. According to one method, this may be accomplished when the user pulls the rotation grip 68 in the proximal direction to translate the central shaft 64 proximally relative to the lower shaft 62 and reduction legs 66. As described above, this causes the interior surfaces and tapers of the reduction legs to realign relative to the functional distal end 71 of the central shaft 64 and expand outward relative to the longitudinal axis of the central shaft. Alternatively, according to a second method, the central shaft is moved proximally relative to the lower shaft 62 and reduction legs 66 when the user rotates the reduction grip 54 to translate the thread upper shaft distally relative to the connector, translating the lower shaft 62 and reduction legs 66 with it. Initially, the central shaft 64 may also translate distally with the reduction shaft 58 until it encounters the fixation rod (i.e., the lock screw interface 70 and/or the locking screw contact the fixation rod), at which point the rod 14 stops the central shaft from further translation and the interior surfaces and tapers of the reduction legs 66 again realign relative to the functional distal end 71 of the central shaft 64 and expand outward relative to the longitudinal axis of the central shaft. With the reduction legs expanded, the user begins or continues to rotate the reduction grip 54 which causes the reduction shaft to translate distally relative to the guide assembly 16 and the fixation rod 14, drawing the rod 14 and bone anchor 12 together. Once the fixation rod 14 is fully seated, the rotation grip 68 is used to rotate the central shaft and engage the lock screw into the anchor housing. Once the rod 14 is fully captured by the lock screw the reducer 40 can be disengaged from the guide 16. The central shaft can be moved distally allowing the reduction legs 66 to return to the contracted position so the distal end of the reduction shaft can pass through the proximal end of the guide. The angled surfaces 115 on the reduction legs 66 may engage to guide 16 during removal to ensure the reduction legs do return to the contracted position for removal. The lock screw may be further tightened if necessary through the guides 16 which may then be removed, leaving the spinal fixation construct 10 in place.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. .sctn. 1.77 or otherwise to provide organizational queues. These headings shall not limit or characterize the invention(s) set forth herein.

What is claimed is:

1. A minimally invasive method of reducing a rod into a bone anchor, comprising:
   introducing the rod into a guide channel of a guide assembly, the guide assembly being coupled to the bone anchor;
   coupling a proximal end of the guide assembly to a connector of a reducer, the reducer including:
      the connector;
      a reduction shaft comprising an upper shaft with exterior threading, a lower shaft coupled to the upper shaft, and a pair of reduction legs at or near a distal end of the lower shaft, the pair of reduction legs being movable between a contracted position and an expanded position,
         wherein in the contracted position, the pair of reduction legs have an effective diameter that approximates a diameter of the reduction shaft, and in the expanded position, the pair of reduction legs extends beyond a distal end of a central shaft;
      the central shaft positioned at least partly within a hollow bore of the reduction shaft, the central shaft comprising a rotation grip fixedly attached at or near a proximal end thereof; and
      a reduction grip positioned proximal to the connector, wherein the exterior threading of the upper shaft mates with an interior threading of the reduction grip;
   advancing the reduction shaft in a distal direction through the guide assembly while the pair of reduction legs is in the contracted position;
   fixing a position of the guide assembly and the bone anchor relative to the connector;
   advancing the pair of reduction legs in the distal direction to the expanded position;
   rotating the reduction grip, causing the reduction shaft to translate distally relative to the guide assembly and the rod, and drawing the rod and the bone anchor together.

2. The method of claim 1, further comprising:
   prior to advancing the reduction shaft, coupling a lock screw to a lock screw interface on the distal end of the central shaft, wherein the lock screw interface is configured to engage and hold the lock screw.

3. The method of claim 2, further comprising:
   after drawing the rod and the bone anchor together, rotating the central shaft using the rotation grip, thereby engaging the lock screw into a housing of the bone anchor.

4. The method of claim 3, further comprising:
   disengaging the reducer from the guide assembly after engaging the lock screw into the housing of the bone anchor.

5. The method of claim 4, wherein the disengaging further comprises translating the central shaft in the distal direction, thereby allowing the pair of reduction legs to return to the contracted position, and a distal end of the reduction shaft can pass through the proximal end of the guide assembly.

6. The method of claim 4, wherein an angled surface on each reduction leg in the pair of reduction legs engages the guide assembly during the disengaging, thereby ensuring that the pair of reduction legs returns to the contracted position for removal of the reducer.

7. The method of claim 4, further comprising: after disengaging the reducer from the guide assembly, tightening the lock screw through the guide assembly.

8. The method of claim 7, further comprising removing the guide assembly, leaving the bone anchor and the rod in place.

9. The method of claim 1, wherein the step of advancing the pair of reduction legs further comprises aligning the pair of reduction legs with a rod channel in the guide assembly.

10. The method of claim 1, wherein the step of advancing the pair of reduction legs further comprises advancing the pair of reduction legs past the proximal end of the guide assembly.

11. The method of claim 1, wherein the step of advancing the pair of reduction legs further comprises expanding the pair of reduction legs radially outward relative to a longitudinal axis of the central shaft, thereby increasing the effective diameter of the pair of reduction legs.

12. The method of claim 1, wherein the step of advancing the pair of reduction legs further comprises providing two points of contact on the rod, wherein a first point of contact is between the rod and a first reduction leg of the pair of reduction legs, and a second point of contact is between the rod and a second reduction leg of the pair of reduction legs.

13. The method of claim 1, wherein the step of advancing the reduction shaft further comprises:
advancing the reduction shaft through a central passage of the guide assembly until an engagement feature on the proximal end of the guide assembly is received and locked in a keyed guide cavity within the connector.

14. The method of claim 1, further comprising:
actuating the advancing of the pair of reduction legs by:
translating the rotation grip in a proximal direction, thereby translating the central shaft in the proximal direction relative to the lower shaft and the pair of reduction legs, and causing an interior surface of the pair of reduction legs to expand outward relative to a longitudinal axis of the central shaft.

15. The method of claim 1, further comprising:
actuating the advancing of the pair of reduction legs by:
translating the central shaft in a proximal direction relative to the lower shaft and the pair of reduction legs when rotating the reduction grip to translate the upper shaft distally relative to the connector, translating the lower shaft and the pair of reduction legs with it.

16. A minimally invasive method of implanting a spinal fixation construct, comprising:
implanting a bone anchor into a bone of a subject;
coupling a guide assembly having a guide channel therein, to the bone anchor;
introducing a fixation rod into the guide channel,
coupling a proximal end of the guide assembly to a connector of a reducer, the reducer including:
the connector;
a reduction shaft comprising an upper shaft with exterior threading, a lower shaft coupled to the upper shaft, and a pair of reduction legs at or near a distal end of the lower shaft, the pair of reduction legs being movable between a contracted position and an expanded position,
wherein in the contracted position, the pair of reduction legs have an effective diameter that approximates a diameter of the reduction shaft, and in the expanded position, the pair of reduction legs extends beyond a distal end of a central shaft;
the central shaft positioned at least partly within a hollow bore of the reduction shaft, the central shaft comprising a rotation grip fixedly attached at or near a proximal end thereof; and
a reduction grip positioned proximal to the connector, wherein the exterior threading of the upper shaft mates with an interior threading of the reduction grip;
advancing the reduction shaft in a distal direction through the guide assembly while the pair of reduction legs is in the contracted position;
fixing a position of the guide assembly and the bone anchor relative to the connector;
advancing the pair of reduction legs in the distal direction to the expanded position; and
rotating the reduction grip, causing the reduction shaft to translate distally relative to the guide assembly and the rod, and drawing the rod and the bone anchor together.

17. The method of claim 16, further comprising:
prior to advancing the reduction shaft, coupling a lock screw to a lock screw interface on the distal end of the central shaft, wherein the lock screw interface is configured to engage and hold the lock screw.

18. The method of claim 17, further comprising:
after drawing the rod and the bone anchor together, rotating the central shaft using the rotation grip, thereby engaging the lock screw into a housing of the bone anchor; and
disengaging the reducer from the guide assembly.

19. The method of claim 18, wherein the disengaging further comprises:
translating the central shaft in the distal direction, thereby allowing the pair of reduction legs to return to the contracted position, and a distal end of the reduction shaft to pass through the proximal end of the guide assembly.

20. The method of claim 18, further comprising:
after disengaging the reducer from the guide assembly, tightening the lock screw through the guide assembly; and
removing the guide assembly, leaving the bone anchor and the rod in place.

* * * * *